(12) United States Patent
Milton et al.

(10) Patent No.: US 10,492,768 B2
(45) Date of Patent: Dec. 3, 2019

(54) BIOPSY DEVICE

(71) Applicant: Trevor John Milton, Somerset West (ZA)

(72) Inventors: Trevor John Milton, Somerset West (ZA); Norman Anthony Nieuwenhuizen, Boksburg (ZA)

( * ) Notice: Subject to any disclaimer, the term of this patent is extended or adjusted under 35 U.S.C. 154(b) by 0 days.

(21) Appl. No.: 16/146,287

(22) Filed: Sep. 28, 2018

(65) Prior Publication Data

US 2019/0099168 A1    Apr. 4, 2019

(30) Foreign Application Priority Data

Sep. 29, 2017 (GB) .................................. 1715907.0

(51) Int. Cl.
| | |
|---|---|
| *A61B 10/02* | (2006.01) |
| *A61B 17/3205* | (2006.01) |
| *A61B 17/3209* | (2006.01) |
| *A61B 17/00* | (2006.01) |
| *A61B 17/3211* | (2006.01) |
| *A61B 50/30* | (2016.01) |
| *A61B 17/322* | (2006.01) |
| *A61B 90/00* | (2016.01) |

(52) U.S. Cl.
CPC ...... *A61B 10/0266* (2013.01); *A61B 17/3205* (2013.01); *A61B 17/32093* (2013.01); *A61B 50/3001* (2016.02); *A61B 17/322* (2013.01); *A61B 2010/0208* (2013.01); *A61B 2017/0042* (2013.01); *A61B 2017/00761* (2013.01); *A61B 2017/00862* (2013.01); *A61B 2017/32113* (2013.01); *A61B 2090/08021* (2016.02)

(58) Field of Classification Search
CPC ........ A61B 10/0266; A61B 2010/0208; A61B 17/3205; A61B 17/32093; A61B 17/322; A61B 2017/00761; A61B 2017/32113; A61B 2017/0042; A61B 50/3001
See application file for complete search history.

(56) References Cited

U.S. PATENT DOCUMENTS

| | | | |
|---|---|---|---|
| 4,943,295 A | | 7/1990 | Hartlaub et al. |
| 5,344,424 A | * | 9/1994 | Roberts .............. A61B 17/3213 30/162 |

(Continued)

FOREIGN PATENT DOCUMENTS

| | | |
|---|---|---|
| EP | 2865345 | 4/2015 |
| JP | 2008/061869 | 3/2008 |

OTHER PUBLICATIONS

Combined Search and Examination Report dated Oct. 27, 2017, issued in Great Britain application (No. GB1715907.0).

(Continued)

*Primary Examiner* — Devin B Henson
(74) *Attorney, Agent, or Firm* — Womble Bond Dickinson (US) LLP (57) ABSTRACT

A handheld biopsy device is provided which includes an elongate base having a slider movable relative thereto between a stowed condition and at least one operative condition. An elongate blade which is resiliently flexible in its length is secured between the base and the slider such that with the slider in the stowed condition the blade extends generally parallel to the base, and with the slider in the at least one operative condition the blade flexes away from the base into a bowed shape.

17 Claims, 6 Drawing Sheets

(56) References Cited

U.S. PATENT DOCUMENTS

| | | |
|---|---|---|
| 5,794,626 A | 8/1998 | Kieturakis |
| 6,022,362 A | 2/2000 | Lee et al. |
| 8,931,379 B2 * | 1/2015 | Allyn .................... A61B 10/02 30/51 |
| 2014/0107687 A1 | 4/2014 | Allyn |
| 2017/0055960 A1 | 3/2017 | Kattine et al. |

OTHER PUBLICATIONS

Extended European Search Report dated Feb. 14, 2019, issued in European application (No. 18197723.2).

* cited by examiner

BIOPSY DEVICE

FIELD OF THE INVENTION

This invention relates to a biopsy device, more particularly to a handheld device suitable for skin biopsies.

BACKGROUND TO THE INVENTION

It is often required to remove skin lesions from a patient. These may either be disposed of or sent for a biopsy. One method commonly used to remove skin lesions is referred to as a shave biopsy. To conduct a shave biopsy a practitioner will frequently use an elongate blade which is flexible in its length which is bowed by the user by pinching it gently between thumb and forefinger. Double-edged razor blades which have been split lengthwise in half have been widely used for this purpose. However, the potential of breaking the blade when splitting it, and the potential of the user being inadvertently cut while using the blade have led to devices being produced which essentially provide either grips or holders for razor blades or which make use of purpose-built blades. Such devices still require the user to pinch the grip or holder to cause the blade to bend.

A feature shared by all shave biopsy devices which make use of a blade which is bent by the user is that the user must exert a bending pressure on the blade while simultaneously exerting a cutting action on the patient's skin. The cutting action may include sliding the blade forward and a side to side sawing motion. This procedure can be awkward when the lesion is in a difficult to reach position on the patient. Furthermore, as the pressure exerted by the user can vary during the procedure, the arc of curvature of the blade can also vary during the procedure. There is also the risk that the blade becomes inverted and instead of bowing outwardly away from the user's hand, it bows inwardly towards the user's hand. This is undesirable if it occurs during the procedure and can also pose a risk to the user.

Also, there is a risk of the user being accidentally cut by the blade before and after using it as the edge generally remains exposed.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided a handheld biopsy device comprising a base having a slider movable relative thereto between a stowed condition and at least one operative condition, and an elongate blade which is resiliently flexible in its length and secured between the base and the slider such that with the slider in the at least one operative condition the blade flexes away from the base into a bowed shape.

Further features of the invention provide for the blade to have a sharp edge which is shielded in the stowed condition; for the blade to extend generally parallel to the base with the slider in the stowed condition; for the blade to be secured to a flexible retainer; for the blade to locate over pins extending from the retainer and for a tab to secure the blade over each pin; for the slider to extend from one end of the retainer; for the opposite end of the retainer to be hingedly secured to the base; and for the retainer to be integrally moulded with the base.

Still further features of the invention provide for the blade to have a single edge; for the blade to be generally complementary to the base; for the base to be elongate and to include at least one finger grip; for the at least one finger grip to include finger grips provided at opposite ends of the base and/or a finger grip in the form of a flange extending from a rear of the base; and for the finger grips provided at opposite ends of the base to include a lip extending upwardly from the base at each end to provide finger grips.

Yet further features of the invention provide for the slider to run in a slot in the base; for the slider to include a button configured to provide finger purchase; for there to be three operative conditions for the slider and for each operative condition to be associated with a different degree of flexing of the blade; for each operative condition to be denoted by a stop position between the slider and the base; and for each stop position to be denoted by a cooperating tooth and notch.

Further features of the invention provide for a disposal condition to be provided for the slider in which the blade is locked in the stowed condition; for a guard to extend over the edge of the blade in the stowed condition; and for the guard to be provided by a lip extending from the base.

An embodiment of the invention will now be described, by way of example only, with reference to the accompanying drawings.

DETAILED DESCRIPTION WITH REFERENCE TO THE DRAWINGS

A handheld biopsy device is provided and includes a base having a slider movable relative thereto. The base may be elongate and the slider may run in a slot extending in a lengthwise direction in the base. The slider may also extend from one side of the base and run in grooves or a channel formed in or on the base. The slider is movable between a stowed condition and at least one operative condition. The slider may be slidably movable or may move about a pivot.

Finger grips may be provided at opposite ends of the base and a further grip may also be provided on the base to allow a user to hold and manipulate the device by hand. The further grip may include a flange which extends from the base.

An elongate blade which is resiliently flexible in its length is secured between the base and the slider such that with the slider in the stowed condition the blade is generally planar or flat and with the slider in the at least one operative condition the blade flexes away from the base into a bowed shape. In the stowed condition, the blade may extend generally parallel to the base generally or may be positioned relative to the base in a manner in which it is shielded or generally inaccessible to inadvertent contact, and may conform generally to a surface of the base. Alternatively, the blade may be slightly bowed in the stowed condition and its sharp edge preferably shielded or protected from contact, such as by a guard.

The blade may have a single edge and its shape may be generally complementary to the base.

The blade may be secured to a flexible retainer. The retainer may include pins over which corresponding apertures in the blade may locate. Tabs which are securable to the retainer may be used to secure the blade in position over the pins. Alternatively the pins may be deformed, such as through ultrasonic welding or heating, to secure the blade in position.

The retainer may be hingedly secured to the base, preferably at one end thereof. Conveniently, the retainer may be moulded integrally with the base with a hinge provided therebetween. Any suitable plastics material can be used, with preference given to those materials which can be easily sterilised for use in healthcare applications.

The slider may be carried on the retainer. Conveniently, the slider may be moulded integrally with the retainer and provided on a folding flap or hinge opposite the hinge with the base.

The blade may also be directly secured, preferably hingedly, at or near one end to the base and directly secured, preferably hingedly, at or near the opposite or second end to the slider.

Three operative conditions may be provided for the slider and hence for the blade. The different operative conditions are selected to cause more or less bending of the blade and so to obtain bowed shapes which are more or less acute. Each operative condition is thus associated with a different degree of flexing or bowing of the blade. Each operative condition may be denoted by a stop position between the slider and the base, and each stop position may be denoted by a cooperating tooth and notch. A tooth may be provided on the slider and V-shaped notches, or notches with inclined edges, formed in a side of the slot or adjacent thereto in which the tooth can locate to at each stop position.

Furthermore, a disposal condition may be provided for the slider. In the disposal condition the blade may be locked in a stowed condition in which it extends generally parallel to the base with its edge shielded or protected from external contact by a guard. The guard may be provided by a lip extending normally from the base. Once the slider has been moved to the disposal condition it may no longer be possible to move it to one of the operative conditions.

One embodiment of a skin biopsy device (1) is shown in FIGS. 1 to 5 and includes an elongate, generally planar, rectangular base (3) moulded from a plastics material. A lip (5) extends upwardly from the base (3) at each end (7, 9) to provide finger grips, and a co-planar flange (11) extends from the rear (13) of the base (3) from adjacent the end (7) to approximately two thirds along the length thereof. The flange (11) provides a further finger grip and has a grooved or textured surface to enhance grip.

Figure 1:
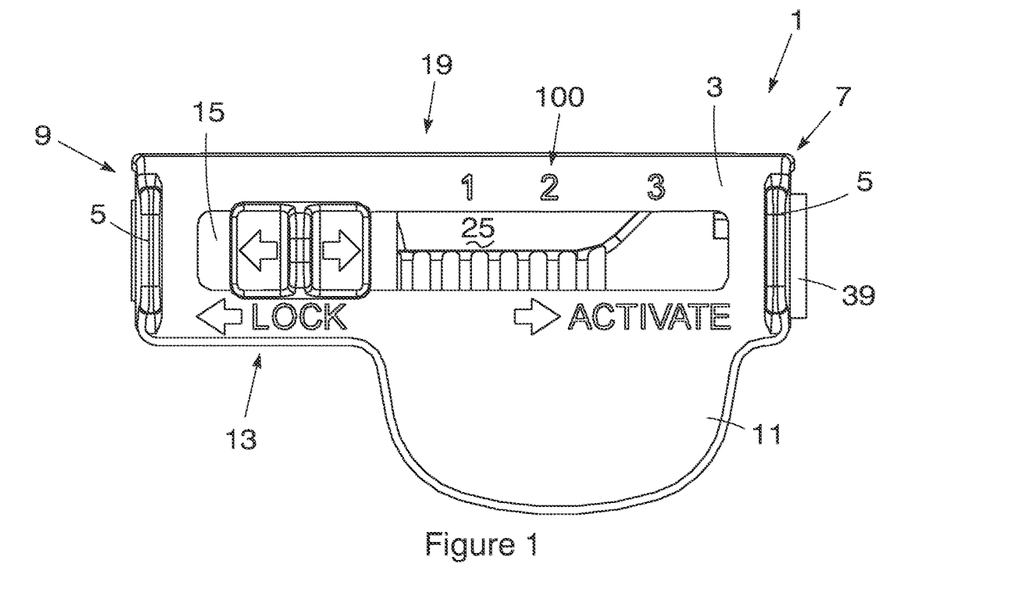
FIG. 1 is a top plan view of a skin biopsy device.
Figure 2:
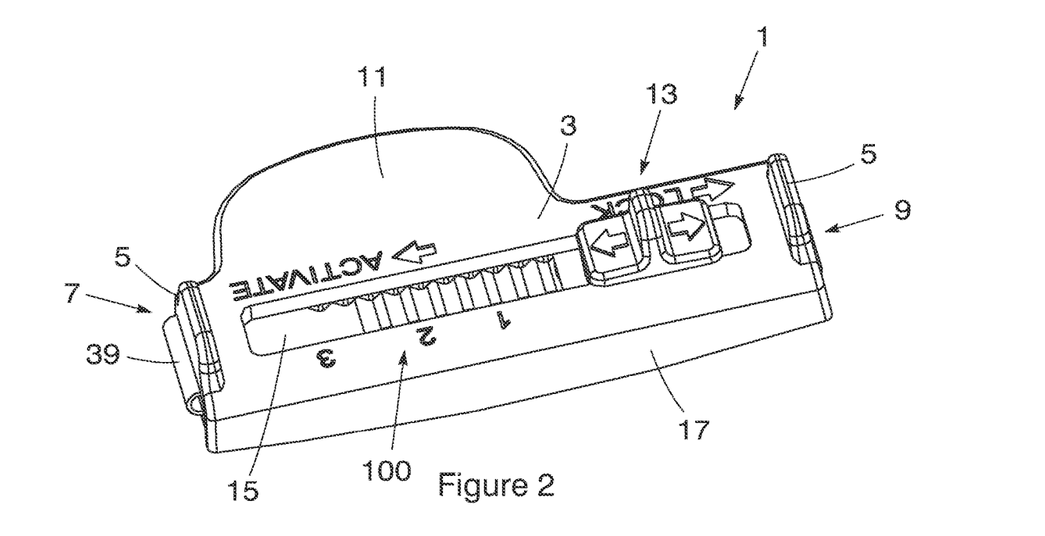
FIG. 2 is a three-dimensional top view of the device in FIG. 1.
Figures 3, 4:
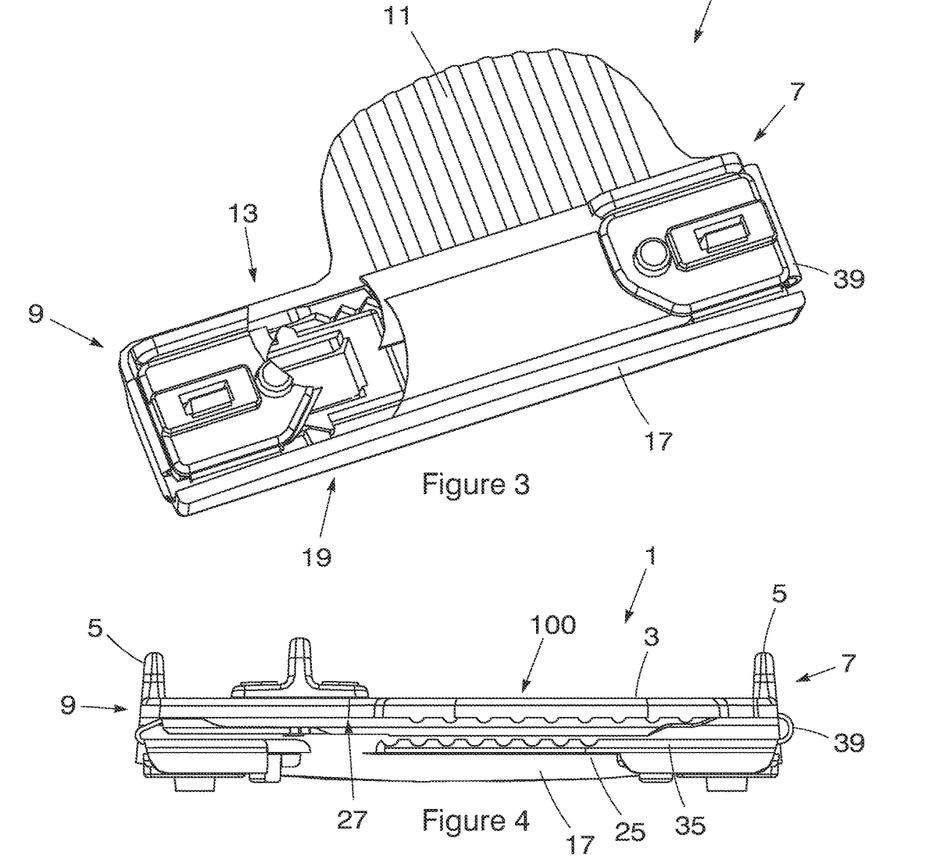
FIG. 3 is a three-dimensional bottom view of the device in FIG. 1.
FIG. 4 is a rear elevation of the device in FIG. 1.
Figure 5:
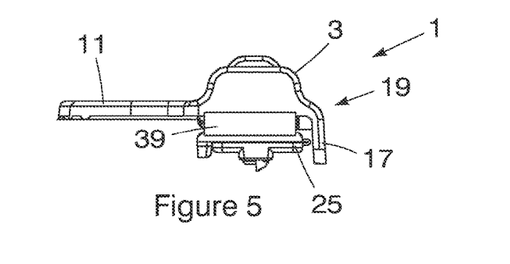
FIG. 5 is a side elevation of the device in FIG. 1.

A rectangular slot (15) extends centrally along the base (3) between its ends (7, 9) and a downwardly extending lip (17) is provided along the front (19) of the base (3).

Figure 6:
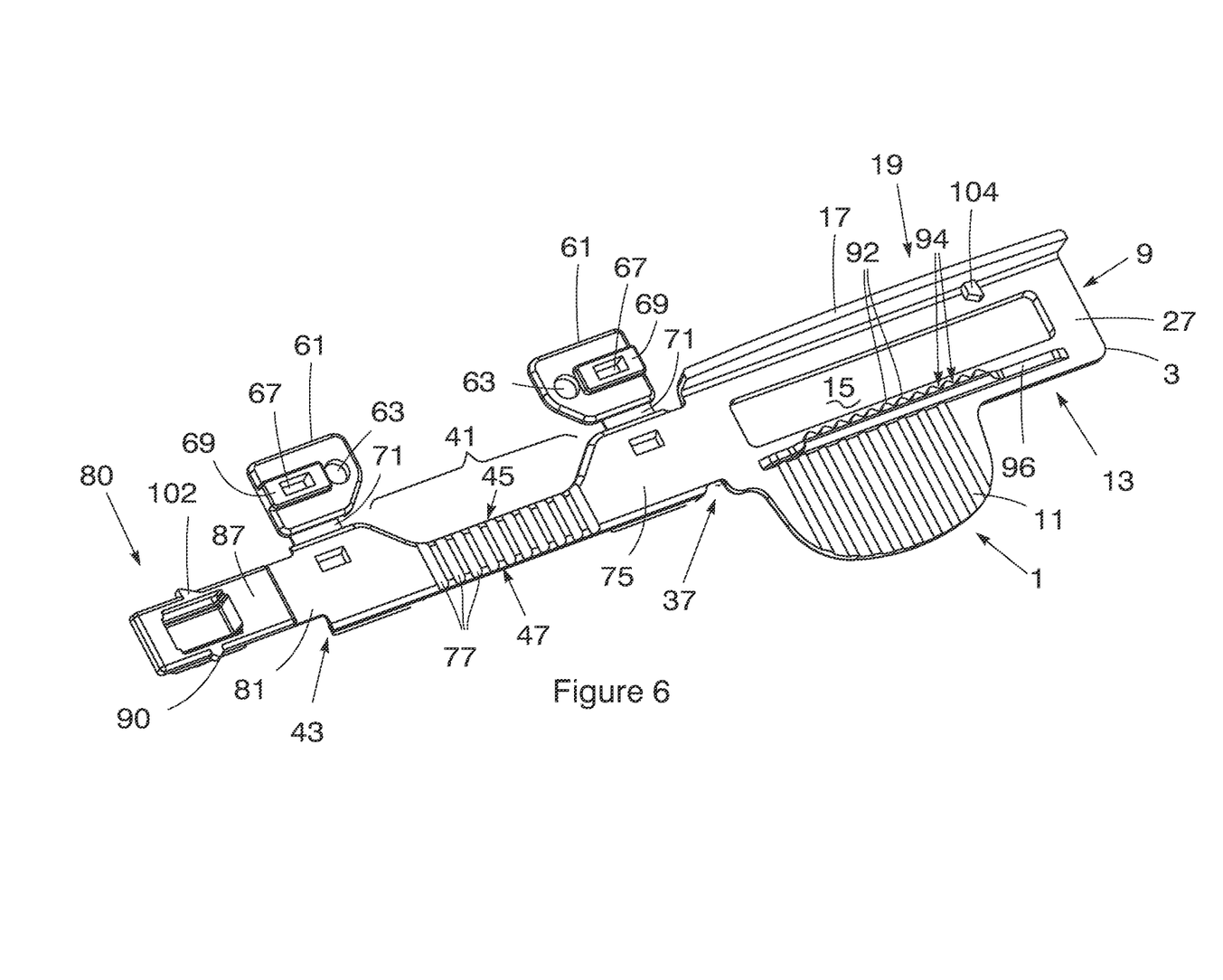
FIG. 6 is a three-dimensional bottom view of the device in FIG. 1 in a disassembled condition and without a blade.
Figures 7, 8:
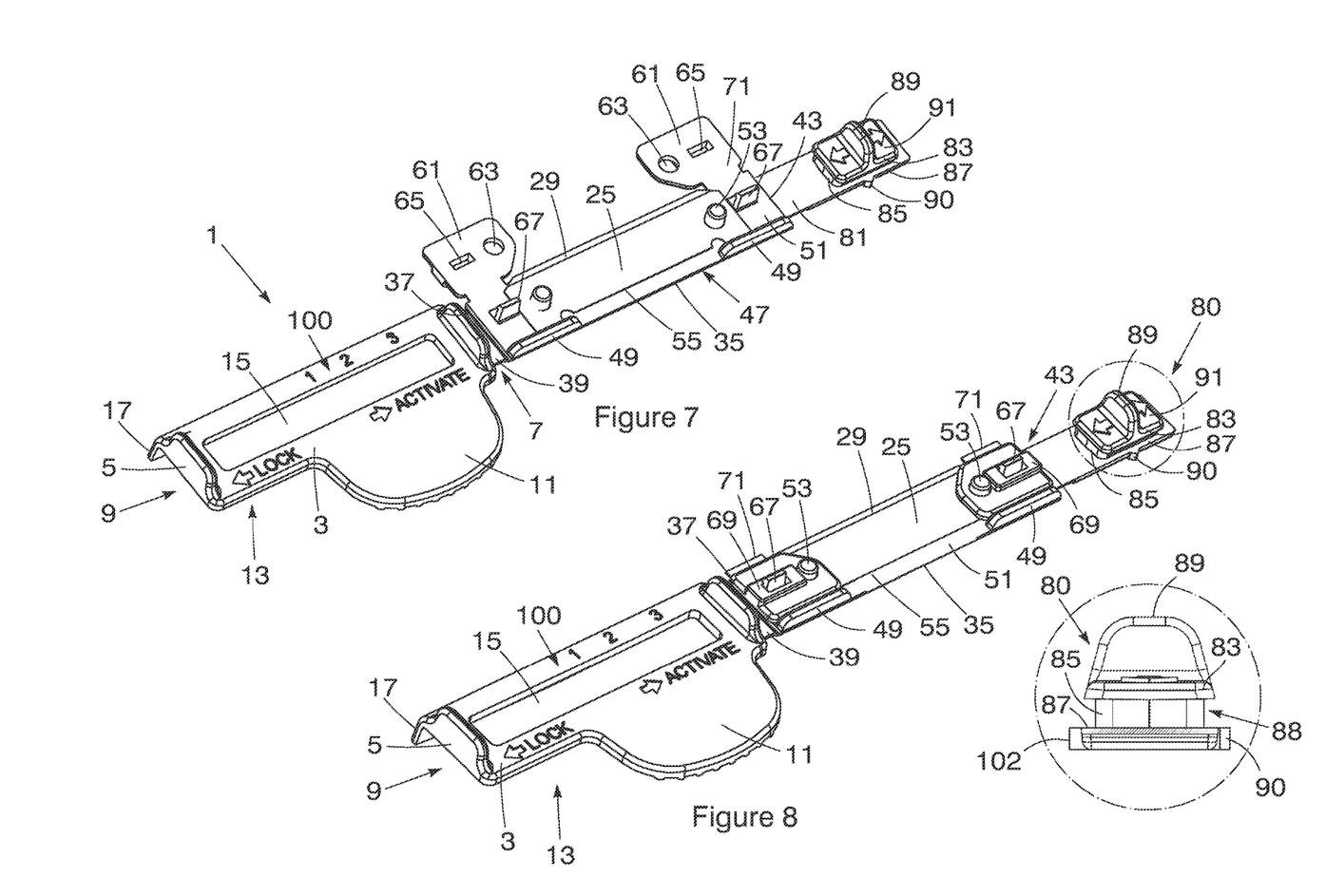
FIG. 7 is a three-dimensional top view of the device in FIG. 1 in a disassembled condition.
FIG. 8 is a three-dimensional top view of the device in FIG. 1 in a partially assembled condition.
Figure 9:
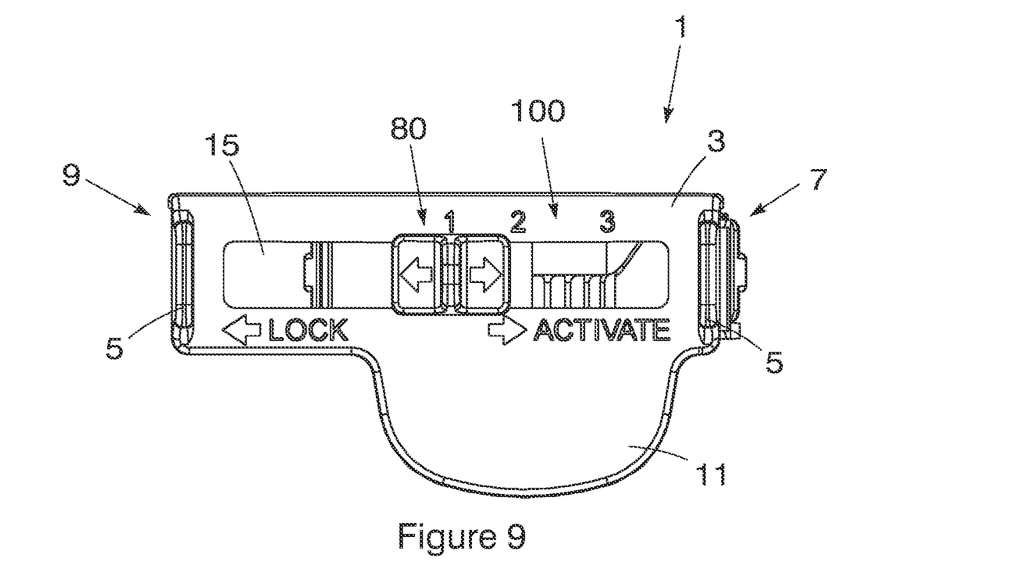
FIG. 9 is a top plan view of the device in FIG. 1 in an operative condition.
Figure 10:
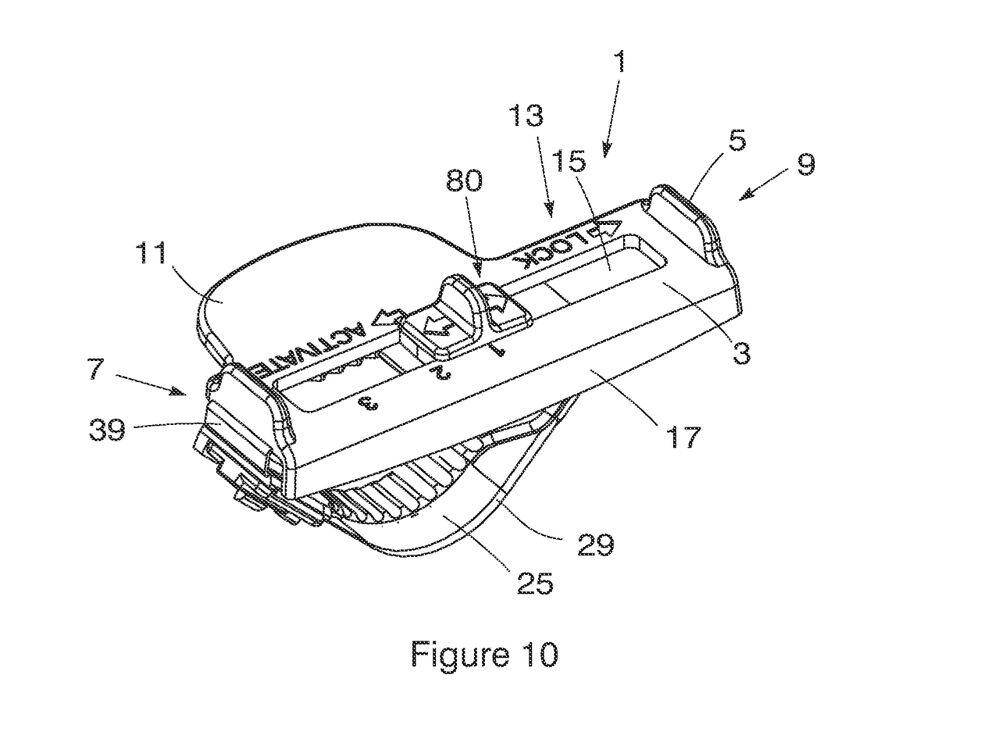
FIG. 10 is a three-dimensional top view of the device in FIG. 9.
Figures 11, 12:
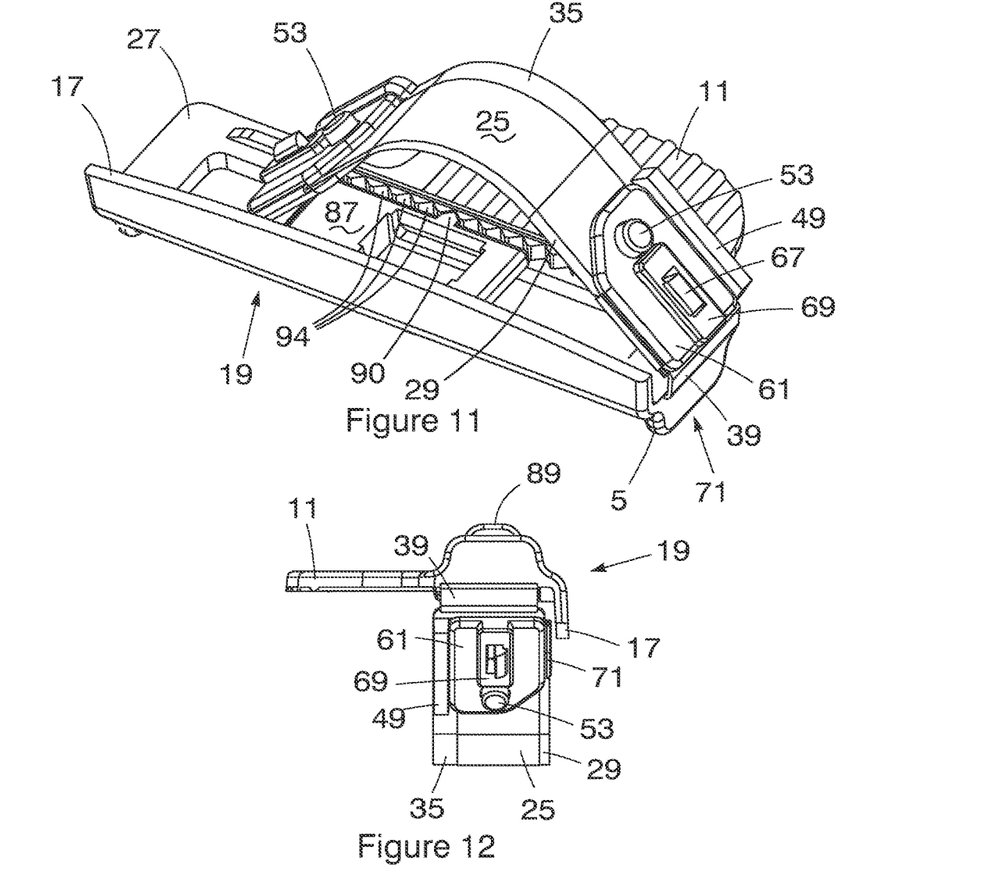
FIG. 11 is a three-dimensional bottom view of the device in FIG. 9.
FIG. 12 is a side elevation of the device in FIG. 9.

An elongate resiliently flexible blade (25) is provided adjacent the bottom (27) of the base (3). As shown more clearly in FIGS. 6 to 8, in this embodiment, the blade (25) has a single sharpened edge (29) (commonly referred to as a single edged blade) which extends substantially across its length and is arranged to face in the direction of the lip (17) along the front (19) of the base (3). The blade (25) is secured to an elongate flexible retainer (35) which is hingedly secured at one end (37) to the end (7) of the base (3). In this embodiment, the base (3) and retainer (35) are moulded integrally with a hinge (39) between them. The retainer (35) is generally rectangular with a waist (41) provided between its ends (37, 43) which extends from its front (45) towards its rear (47). A pair of ridges (49) extend from the bottom (51) of the retainer (35) along the rear (47), one from each end (37, 43) a short distance towards the centre. A pair of pins (53) extend normally from the bottom (51) of the retainer (35) generally centrally of its width and each spaced apart from an end (37, 43). Corresponding apertures (not shown) are provided in the blade (25) to permit it to be located over the pins (53) with its rear edge (55) abutting the ridges (49). The blade (25) is secured to the retainer (35) by a pair of tabs (61), each of which has an aperture (63) which locates over a pin (53) with the blade (25) between the retainer (35) and the tab (61). A slot (65) is provided in each tab (61) and provides a snap fit over a toothed lug (67) extending normally from the bottom (51) of the retainer (35) between each pin (53) and its corresponding end (37, 43). A reinforcing collar (69) extends around each slot (65) on the side opposite the blade (25). As illustrated in FIGS. 6 and 7, in this embodiment, each tab (61) is moulded integrally with the retainer (35) with a hinge (71) between them. This permits the retainers (61) to simply be folded over the blade (25) and pins (53) to be secured to the toothed lugs (67), as illustrated in FIG. 8.

The top (75) of the retainer (35) has a series of parallel grooves (77) extending across its width along the length of the waisted section (41) to facilitate bending of the retainer (35) in its length.

When the blade (25) is secured to the retainer (35) its sharp edge (29) extends slightly beyond the front (45) of the retainer (35).

A slider (80) extends from hinge (81) at the end (43) of the retainer (35) opposite the base (3). The slider (80), hinge (81) and retainer (35) are moulded integrally with each other in the same way that the retainer (35), hinge (39) and base (3) are moulded integrally with each other. Apart from the blade, the entire device is thus moulded as a single piece in this embodiment.

The slider (80) includes a rectangular button (83) carried on a central, inwardly recessed pillar (85) which extends from an elongate, plate-like body (87) which is slightly wider than the button (83). A channel (88) is formed between the button (83) and body (87) as a result of the recessed pillar (85). A ridge (89) extends centrally across the top (91) of the button (83) to provide finger purchase.

With the blade (25) secured to the retainer (35) the device (1) is finally assembled by folding the slider (80) about the hinge (81) so that the body (87) lies adjacent the bottom (51) of the retainer (35). Next, the retainer (35) is folded about the hinge (39) towards the bottom (27) of the base (3). The button (83) of the slider (80) is then pressed through the slot (15) in the base (3), the sides of which deform outwardly until they are able to provide a snap fit over the pillar (85) and locate in the channel (88) between the button (83) and the body (87). The pillar (85) is of slightly narrower width than the slot (15) which enables the slider (80) to slide along the length of the slot (15).

A trapezoidal or triangular tooth (90) extends laterally from one side of the body (87) in line with the ridge (89) on the button (83) and cooperates with the inclined edges (92) of notches (94) provided on an associated side of an elongate rib (96) extending from the bottom (27) of the base (3) adjacent the slot (15). The arrangement is such that as the slider (80) is moved in the slot (15) the tooth (90) sequentially engages with the notches (94) and will form a "click-stop" in each position. A person operating the slider will be able to feel the sequential "click-stops" and, with appropriate design, also hear them. Markings "1", "2" and "3" are provided on the top (100) of the base (3) corresponding with sequential "click-stops" to provide a visual indication of the position of the slider (80). However, the tooth (90) in cooperation with the notches (94) afford positive intermediate positioning in addition to the three marked operative positions.

A ramped tooth (102) extends laterally from the body (87) opposite the tooth (90) and is shaped to engage a similarly ramped detent (104) extending from the lip (17) along the bottom (27) of the base (3) towards the slot (15) near the end (9). The arrangement is such that continued movement of the slider (80) towards the detent (104) causes the ramped surfaces of the tooth (102) and detent (104) to engage and eventually slide over each other until the tooth (102) is captured behind the detent (104). This locks the slider (80) in position in the slot (15) at the end (9) and prevents it from being moved back towards the opposite side of the slot (15).

In use, the skin biopsy device (1) is supplied with the slider (80) in a stowed condition adjacent the end (7) of the slot (15), as shown in FIGS. 1 to 5. The resilience of the blade (25) and retainer (35) provide a bias which maintains both in this condition in which the blade (25) extends generally parallel to the base (3) on the retainer (35) with its sharp edge (29) shielded by the lip (17) which acts as a guard. The device can be handled safely in the stowed condition without fear of the user being inadvertently cut by the blade (25) as its sharp edge (29) is effectively inaccessible.

Referring to FIGS. 9 to 13, to use the device (1) the slider (80) is moved in the slot (15) against the bias provided by the blade (25) and retainer (35) to an operative condition indicated by the markings. Engagement of the tooth (90) with the notches (94) will also result in audible and tactile feedback. Movement of the slider (80) towards the end (7) of the base (3) causes the retainer (35), which is secured through the hinge (39) at one end (37) to the base (3) and at the other end (43) through the hinge (81) to the slider (80), to flex outwardly away from the base (3). The blade (25), being secured to the retainer (35), is similarly outwardly flexed and assumes a bowed shape. The further the slider (80) is moved towards the end (7) the more acute the bowing, or bending, of the blade (25) becomes, as shown more clearly in FIG. 13. The degree of bowing of the blade (25) is thus governed or dictated by the position of the slider (80) in the slot (15).

Figure 13:
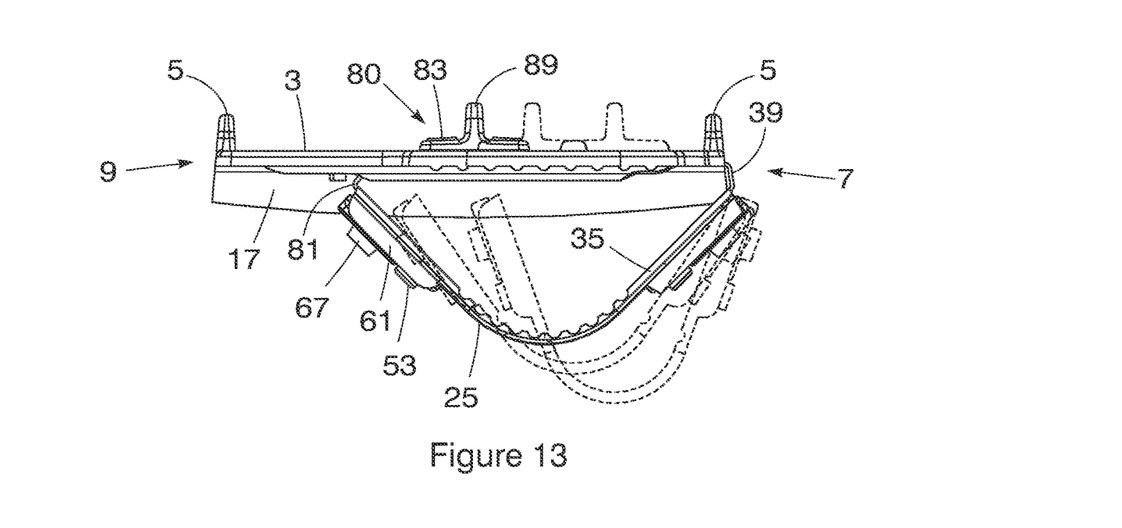
FIG. 13 is a rear elevation of the device in FIG. 9 showing further operative conditions for the blade.

It will be appreciated that the hinges (39, 81) serve an important function in not only securing the base (3) and slider (80) to the retainer (35) but also in permitting the linear motion of the slider (80) to be effectively transmitted into flexing or bowing of the blade (25) by enabling the ends (37, 43) of the retainer to pivot outwardly with respect to the base (3) and slider (80) respectively.

The hinge (39) also facilitates movement of the slider (80) to the disposal condition in that it assists in permitting the tooth (102) to slide over the detent (104) and be captured behind it.

The markings denote convenient, easily repeatable, operative conditions for the blade (25) which permit a user to obtain the same degree of bowing on different devices. As indicated above, the tooth (90) in cooperation with the notches (94) affords positive intermediate positioning in addition to the three marked operative positions.

The cooperating tooth and notches maintain the blade in the selected condition leaving the user's fingers free to grip and manipulate the base using either the lips (5) at either end (7, 9) or the flange (11). The ability of the user to hold the device in two different ways, and thus be able to exercise two different grips on it, provides a further important advantage in that it provides an added degree of flexibility in use. The user is thus not constrained to a single grip which may be difficult to exercise in certain circumstances or positions, and is instead permitted to use a more intuitive grip. For example, where a sliding action along the skin is required, gripping the device using the lips (5) may be convenient. However, where a scooping or gouging action is required it may be more convenient to grip the flange (11).

A less acute degree of bowing, in this embodiment denoted by the operative condition marked "1", may be selected when a relatively large biopsy is required, and a more acute degree of bowing, denoted by the operative conditions marked "2" or "3", may be selected when a smaller or more precise biopsy is required. Intermediate positions may also be selected if desired. The user thus has the convenience of preselecting or moving between operative conditions and does not have to control the degree of bowing while at the same time conducting the biopsy.

Once the procedure has been completed and it is desired to dispose of the device the slider is moved back towards the end (9) and its stowed condition in which the blade (25) is once more shielded by the lip (17). The stowed condition will generally be felt by the user as the ramped tooth (102) engages the detent (104). Further movement of the slider (80) against the resistance provided by the detent (104) causes the ramped tooth (102) to slide over the detent (104) and the slider to be locked in position against the end (9) of the slot (15). This may be termed a locked or disposal condition. In this disposal condition the slider, and hence the blade, can no longer be operated and the blade is safely obstructed from inadvertent, or even advertent, contact with anyone subsequently handling the device. The skin biopsy device may thus be safely disposed of when in the disposal condition without any special precautions having to be taken and using standard medical waste procedures.

The skin biopsy device is both safe and easy to use, and permits the user to concentrate on the procedure without being distracted by having to bend or bow the blade and at the same time avoiding inadvertent contact with its sharp edge. Furthermore, the device can be cost effectively manufactured and easily assembled.

The materials used will clearly be selected to permit appropriate sterilisation of the device.

It will be appreciated that many other embodiments of a skin biopsy device exist which fall within the scope of the invention particularly as regards its configuration and operation. For example, the blade may be secured to the base and be operable through slider in any convenient manner. The blade need not be secured to a retainer but could, for example, be secured at its ends between the base and slider, and the slider could make use of a cam or other suitable means for causing the blade to flex. Any suitable materials can be used in the construction of the base, slider and blade.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A handheld biopsy device, comprising:
  a base having a slider that is movable along a slot in the base between a stowed condition and at least one operative condition; and
  an elongate blade which is resiliently flexible in its length and is secured to a flexible retainer,
  wherein the flexible retainer is hingedly secured at one end of the base and the slider extends from an opposite end of the flexible retainer, and
  wherein the slider is configured to be moved along the slot to the at least one operative condition to flex the blade away from the base into a bowed shape.

2. A handheld biopsy device as claimed in claim 1 the blade extends generally parallel to the base with the slider in the stowed condition.

3. A handheld biopsy device as claimed in claim 1, in which the blade locates over pins extending from the flexible retainer and a tab secures the blade over each pin.

4. A handheld biopsy device as claimed in claim 1 in which the flexible retainer is integrally moulded with the base.

5. A handheld biopsy device as claimed in claim 1 in which the blade has a single edge.

6. A handheld biopsy device as claimed in claim 1 in which the base is elongate and includes at least one finger grip.

7. A handheld biopsy device as claimed in claim 6, wherein the at least one finger grip includes finger grips provided at opposite ends of the base and/or a finger grip in the form of a flange extending from a rear of the base.

8. A handheld biopsy device as claimed in claim 7, wherein the finger grips provided at opposite ends of the base include a lip extending upwardly from the base at each end to provide finger grips.

9. A handheld biopsy device as claimed in claim 1 in which the slider runs in the slot in the base.

10. A handheld biopsy device as claimed in claim 1 in which the slider includes a button configured to provide finger purchase.

11. A handheld biopsy device as claimed in claim 1 in which the slider has three operative conditions and each operative condition is associated with a different degree of flexing of the blade.

12. A handheld biopsy device as claimed in claim 11 in which each operative condition is denoted by a stop position between the slider and the base.

13. A handheld biopsy device as claimed in claim 1 in which a disposal condition is provided for the slider in which the blade is locked in the stowed condition.

14. A handheld biopsy device as claimed in claim 1 in which a guard extends over an edge of the blade in the stowed condition.

15. A handheld biopsy device, comprising:
  a base having a slider that is movable along a slot in the base between a stowed condition and at least one operative condition; and
  an elongate blade which is resiliently flexible in its length and is secured to a flexible retainer,
  wherein the flexible retainer is hingedly secured at one end of the base and the slider extends from an opposite end of the flexible retainer,
  wherein the slider is configured to be moved along the slot to the at least one operative condition to flex the blade away from the base into a bowed shape, and
  wherein the base includes a detent configured to lock the slider in a locked condition in which the slider can no longer be operated and the blade is obstructed.

16. A handheld biopsy device, comprising:
  a base having a slot in which a slider is movable between a stowed condition and at least one operative condition;
  a finger grip in the form of a flange extending from a rear of the base; and
  an elongate blade which is resiliently flexible in its length and is secured to a flexible retainer,
  wherein the flexible retainer is moulded integrally with the base with a hinge provided therebetween and the slider is provided at an end of the flexible retainer opposite the hinge,
  wherein the slider is configured to be moved along the slot to the at least one operative condition to flex the blade away from the base into a bowed shape, and
  wherein a tooth and cooperating notches are provided between the slider and the slot which are configured to releasably engage to permit the slider to be secured at a plurality of selectable positions along the slot.

17. A handheld biopsy device as claimed in claim 16, wherein the tooth is provided on the slider and the notches are provided in the slot.

* * * * *